(12) United States Patent
Bouvart et al.

(10) Patent No.: US 7,964,762 B2
(45) Date of Patent: Jun. 21, 2011

(54) PRODUCTION OF PROPYLENE AND ETHYLENE FROM BUTANE AND ETHANE

(75) Inventors: Francois Bouvart, Senlis (FR); Walter Vermeiren, Houthalen (BE); Wolfgang Garcia, Waterloo (BE); Alain Chepda, Laone (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 199 days.

(21) Appl. No.: 12/301,742

(22) PCT Filed: May 16, 2007

(86) PCT No.: PCT/EP2007/054765
§ 371 (c)(1),
(2), (4) Date: Jun. 2, 2009

(87) PCT Pub. No.: WO2007/135060
PCT Pub. Date: Nov. 29, 2007

(65) Prior Publication Data
US 2010/0145120 A1    Jun. 10, 2010

(30) Foreign Application Priority Data
May 22, 2006 (EP) ..................................... 06114339

(51) Int. Cl.
*C07C 6/04* (2006.01)
(52) U.S. Cl. ........ 585/330; 585/328; 585/648; 585/643; 585/259
(58) Field of Classification Search .................. 585/330, 585/328, 648, 643, 259
See application file for complete search history.

(56) References Cited

U.S. PATENT DOCUMENTS
5,026,936 A  *  6/1991  Leyshon et al. ............... 585/315
* cited by examiner

*Primary Examiner* — Thuan Dinh Dang (57) ABSTRACT

The present invention relates to a process for the producing propylene and ethylene from a light hydrocarbon stream comprising essentially ethane and butane. The process involves a non-catalytic cracking of ethane and normal-butane followed by a metathesis of ethylene and 2-butene to increase the propylene yield. Optionally the by-produced isobutane is dehydrogenated and subsequently the produced isobutene is converted to other valuable products like di-isobutylene, alkylate for gasoline blending tertiary-butyl-ethers, poly-isobutylene methyl-metacrylate or isoprene.

8 Claims, 10 Drawing Sheets

PRODUCTION OF PROPYLENE AND ETHYLENE FROM BUTANE AND ETHANE

CROSS-REFERENCE TO RELATED APPLICATIONS

This application claims the benefit of PCT/EP2007/054765, filed May 16, 2007, which claims priority from EP 06114339.2, filed May 22, 2006.

FIELD OF THE INVENTION

The present invention relates to a process for producing propylene and ethylene from a light hydrocarbon stream comprising essentially ethane and butane. The process involves a non-catalytic cracking of ethane and normal-butane followed by a metathesis of ethylene and 2-butene to increase the propylene yield. Optionally the by-produced iso-butane is dehydrogenated and subsequently the produced iso-butene is converted to other valuable products like di-isobutylene, alkylate for gasoline blending, tertiary-butyl-ethers, poly-isobutylene, methyl-metacrylate or isoprene.

THE TECHNICAL PROBLEM AND PRIOR ART

Olefins have long been desired as feedstocks for the petrochemical industries. Olefins such as ethylene, propylene and butenes are useful in preparing a wide variety of petrochemicals, including, but not limited to, polymers and methyl-tertiary-butyl-ether. Accordingly, a large number of processes, described in the literature, are directed to the production of olefins.

U.S. Pat. No. 5,523,502 describes an integrated process for the selective production of olefins from hydrocarbons comprising:
(a) cracking a first hydrocarbon feedstock in a deep catalytic cracking process comprising contacting said heavy hydrocarbon feedstock with a solid, acidic catalyst, in a fluidized or moving bed or dense phase transfer line reactor, in the presence of steam to produce a first olefin-containing effluent;
(b) cracking a second hydrocarbon feedstock in a non-catalytic steam cracking process comprising thermally cracking said second hydrocarbon feedstock in the presence of steam in a radiant zone of a thermal cracking furnace to produce a second olefin-containing effluent;
(c) combining said first olefin-containing effluent with said second olefin-containing effluent to produce a mixed olefin-containing effluent for downstream processing;
(d) recycling a portion of said mixed olefin-containing effluent to the steam cracking step (b) as at least a portion of said second hydrocarbon feedstock; and
(e) recovering an effluent of selectively produced olefins from the mixed olefin-containing effluent from the downstream processing step.

In said process the first hydrocarbon feedstock is selected from the group consisting of crude oil, naphtha, distillate, vacuum gas oil, residual oil and mixtures thereof and the second hydrocarbon feedstock comprises a light hydrocarbon feedstock selected from the group consisting of gas oils, naphthas, butanes, propane, ethane and mixtures thereof.

US 2005 0107650 A1 relates to a method of producing propylene from a hydrocarbon feed stream involving the steamcracking of the hydrocarbon and then processing the ethylene that is obtained to produce the propylene. The invention is particularly applicable to a feed stream, which is, all or mostly, ethane. More precisely it relates to a method of producing propylene from ethane comprising the steps of:

a) steamcracking an ethane or primarily ethane feedstock thereby producing a cracking product containing ethylene, hydrogen, ethane, methane, acetylene and C3 and heavier hydrocarbons;

b) treating said cracking product in an ethylene plant recovery section including removing said hydrogen, methane and C3 and heavier hydrocarbons therefrom and converting said acetylene therein primarily to ethylene to thereby produce a treated cracking product containing primarily ethylene and ethane and including fractionating said treated cracking product in a C2 fractionator and obtaining an ethylene fraction and a bottom ethane fraction;

c) recycling said bottom ethane fraction to said steam cracking;

d) reacting by dimerization in a dimerization section a first portion of said ethylene fraction thereby producing a butene-rich stream;

e) reacting by metathesis in a metathesis section the butene in said butene-rich stream with a second portion of said ethylene fraction thereby producing a propylene-rich stream; and f) separating product propylene from said propylene-rich stream.

U.S. Pat. No. 5,026,936 describes a method for the production of propylene which comprises:

(a) cracking a C4 or higher olefin and/or paraffin hydrocarbon over a zeolite catalyst at conditions favoring production of ethylene and propylene to form a mixture comprised of ethylene, propylene and butene,

(b) separating ethylene and butene from the step (a) reaction mixture, (c) metathesizing said separated ethylene and butene from the step (a) reaction mixture to form additional propylene, and (d) recovering propylene formed in step (a) and step (c).

In many countries there are hydrocarbon feedstocks comprised of ethane, propane and butane. Propane has a high value as LPG, therefore it is separated and sold as LPG and the remaining ethane and butane can be converted to ethylene, propylene and higher olefins. Steamcracking of ethane does only produce ethylene; the amount of propylene is often not sufficient to install the required equipment in order to recover the propylene. Steamcracking of propane produces high amounts of ethylene but rather low amounts of propylene; hence the fuel gas (mainly methane) make is high. Fuel gas make can be considered as loss of potential chemical value. Steamcracking of iso-butane results in low ethylene yields, high propylene yields and higher fuel gas make. However, steamcracking of iso-butane results in significant liquid (C5+) products yield that accelerate coking of the furnace coils and require complicated oil quench equipment in order to minimise fouling downstream of the steamcracker furnace. Moreover, steamcracking of iso-butane results in high iso-butene make that is diluted in other hydrocarbons having 4 carbons.

Metathesis reaction between ethylene and butene-2 allows increasing the propylene production of a steamcracker. However, the presence of iso-butene has to be minimised in a metathesis reaction as iso-butene results in heavier hydrocarbons and hence loss of potential butene-2 that can make more propylene. The following show various metathesis reactions:

Several techniques have been proposed to remove iso-butene upstream of a metathesis reactor. A first one is to convert the iso-butene into methyl-t-butyl-ether or ethyl-t-butyl-ether by reaction with methanol or ethanol respectively over acid-type catalysts. The ethers can be used as gasoline components. A second one is to convert iso-butene into oligomers over acid-type catalysts. The oligomers, mainly di-iso-butene can be used as gasoline component, either as such or after hydrogenation. A third one is to distil the C4 fraction in a superfractionator. As the boiling points of iso-butene and 1-butene are very close, this can be done in a catalytic distillation column that converts the 1-butene continuously into 2-butene, the latter being significantly heavier than the iso-butene. Often these techniques to remove iso-butene also remove some of the normal-butenes by chemical conversion or by distillation. This implies a loss of potential normal-butenes that will result in less propylene through the metathesis reaction.

Gas field heavier hydrocarbons consist generally of ethane, propane, butanes and liquid condensate. The butanes consist of both normal-butane and iso-butane. It is much easier to separate iso-butane from normal-butane than separating iso-butene from a mixture of hydrocarbons having 4 carbons.

It is an object of the invention to provide a flexible process for the production of ethylene and propylene from ethane and normal-butane, although the present invention can operate on normal-butane alone.

It would not depart from the scope of the invention to provide a flexible process for the production of ethylene and propylene from normal-butane and propane or from normal-butane and ethane and propane. This can happen when there is an overcapacity of propane on the LPG market.

It is another object of the invention to provide a process to remove the precursor of iso-butene upstream of the steam-cracker by de-isobutanisation of a mixture of butanes. Conventional technology to separate iso-butane from normal-butane yields two enriched streams; the first one containing more iso-butane and the second one containing more normal-butane than in the feed to the unit.

It is another object of the invention to provide a process to increase the proportion of propylene as compared to ethylene.

It is another object of the invention to provide a process to convert recovered iso-butane into iso-butene.

It is another object of the invention to provide a process to convert recovered iso-butene into poly-iso-butene, di-iso-butene, alkylate for gasoline blending, t-butyl-ethers, methyl-metacrylate and into isoprene.

BRIEF DESCRIPTION OF THE INVENTION

The present invention relates to a process for the selective production of olefins from light hydrocarbons comprising:
a) fractionating a butane fraction in a de-isobutanizer to obtain an enriched iso-butane fraction and an enriched normal-butane fraction,
b) cracking said normal-butane fraction and
optionally an ethane fraction,
optionally a propane fraction,
in a non-catalytic cracking zone to produce an olefin rich stream, preferably the ethane fraction, if any, the propane fraction, if any, and normal-butane fractions are cracked in separate non-catalytic cracking zones,
c) treating said olefin rich stream in a separating section comprising:
removing hydrogen and methane,
recovering an ethylene stream,
recovering an ethane stream and recycling said stream to the cracking zone,
recovering a propylene stream,
recovering a propane stream, optionally recycling said stream to the cracking zone,
recovering a C4 stream,
removing the heavies,
d) selectively hydrogenating the dienes and alkynes in the C4 stream produced in step c) into their corresponding olefins,
e) reacting by metathesis in a metathesis section the C4 stream produced in step d) and a part of the ethylene stream produced in step c) to produce propylene,
f) treating the effluent of step e) to recover:
an ethylene stream optionally recycled to the metathesis section,
a propylene stream,
a C4 and heavies stream,
g) optionally treating the C4 and heavies stream produced in step f) which is either hydrogenated, or not-hydrogenated and recycled to the cracking zone optionally through a de-isobutanizer, or recycled directly to the cracking zone,
h) optionally transforming the recovered iso-butane of step a) in iso-butene and subsequently transforming the obtained iso-butene in poly-iso-butene, di-iso-butene, alkylate for gasoline blending, t-butyl-ethers, methyl-metacrylate or either reacted with formaldehyde to make isoprene.

In an embodiment of the invention a normal-butane fraction and an ethane fraction are cracked in the non-catalytic cracking zone. Optionally the normal-butane fraction and the ethane fraction are cracked in two separate non-catalytic cracking zones.

In another embodiment of the invention a normal-butane fraction and a propane fraction are cracked in the non-catalytic cracking zone. Optionally the normal-butane fraction and the propane fraction are cracked in two separate non-catalytic cracking zones.

In another embodiment of the invention a normal-butane fraction, an ethane fraction and a propane fraction are cracked in the non-catalytic cracking zone. Optionally the normal-butane fraction, the ethane fraction and the propane fraction are cracked in three separate non-catalytic cracking zones.

In another embodiment of the invention a light hydrocarbon feedstock comprising essentially ethane, propane and butane is fractionated to obtain a C3 fraction used as LPG, an ethane fraction and a butane fraction. The butane fraction is sent to the cracking zone through the de-isobutanizer, the ethane fraction is sent to the cracking zone.

Although, it is not the essence of the invention, propane can be substituted to butane in case butane would be temporarily in short supply. This would allow the petrochemical complex to continue to operate.

DETAILED DESCRIPTION OF THE INVENTION

Figure 1:
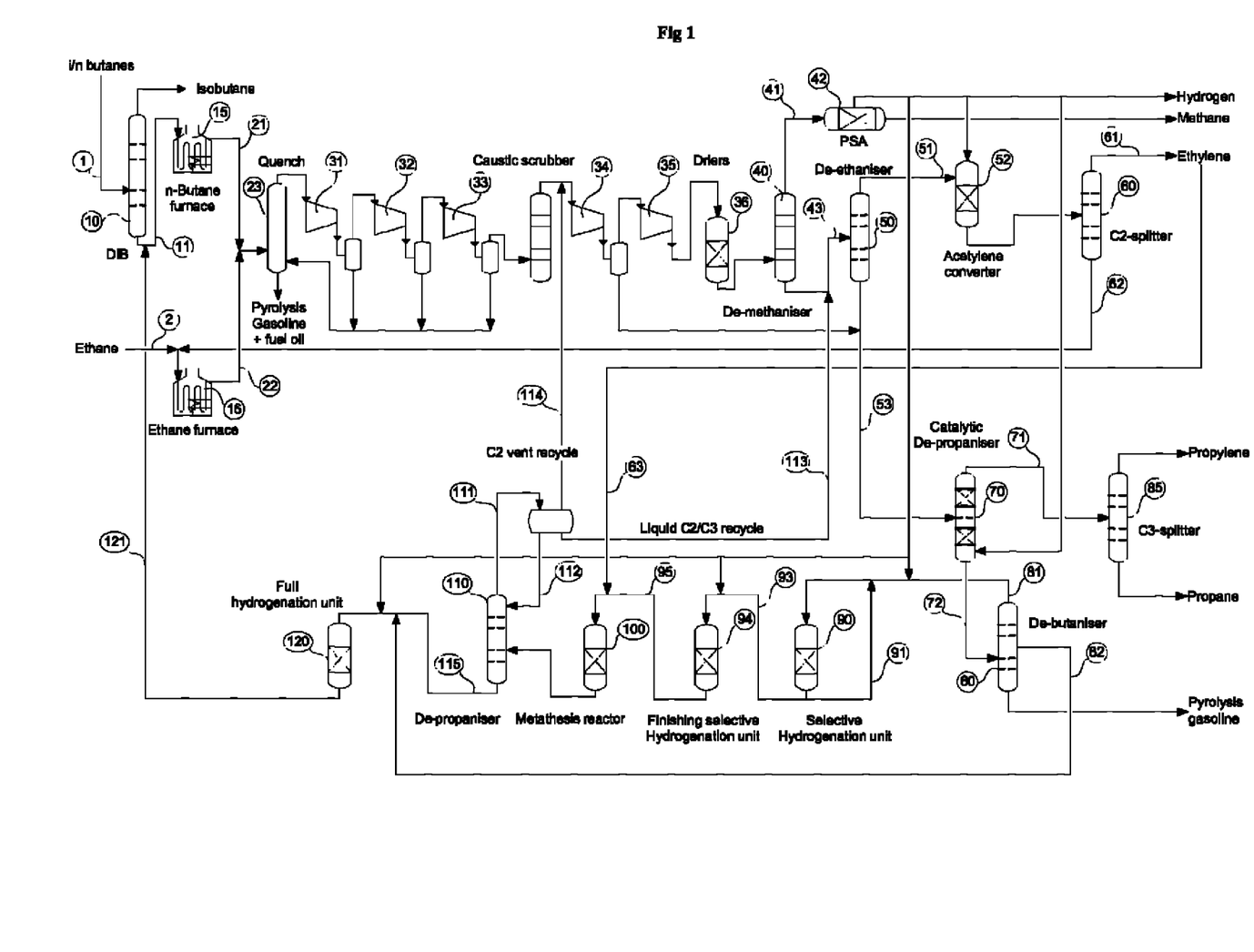

Various flow-schemes of the invention are hereunder described. In these flow-schemes the typical operating pressures of distillation columns are general imposed by a maximum reboiler temperature in order to minimise fouling of the reboiler due to the presence of reactive dienes and alkynes:

De-methaniser: 30-35 bars
De-ethaniser: 22-26 bars
De-propaniser: 12-16 bars
De-butaniser: 3-6 bars
Possible Flow-Schemes:

FIG. 1 is a process flow-scheme illustrating a preferred embodiment of the invention called "De-methaniser first". The various feedstocks involved in the invention as well as their respective products and the steamcracking feed conversions are presented in table 1. Upstream of the cracking furnace the butane mixture is fractionated into a rich iso-butane cut at the overhead and a rich normal-butane cut at the bottom of the distillation column. The non-catalytic cracking of normal-butane results in low iso-butene make. The cracked products are compressed up to about 30-35 bar. The number of compressor stages depends on the refrigerant and its corresponding temperature that is used for condensing the overhead of columns that separate the light hydrocarbons and hydrogen from the heavier hydrocarbons. The raw C4 fraction, produced as overhead of the de-butaniser column is selectively hydrogenated to convert the dienes and alkynes into butenes. This stream is mixed with ethylene and converted over a metathesis catalyst to produce propylene. The product of the metathesis reactor is fractionated in a de-propaniser. The overhead product is cooled down to create reflux stream. Part of the condensed reflux stream can be pumped to the inlet of the de-ethaniser of the steamcracker complex. The light olefin vent stream (C2 vent recycle) can flow to the inlet of the fourth stage compressor of the steamcracker complex that is typically at a pressure of 8 to 12 bars.

Referring to FIG. 1 a raw butane stream comprising iso and normal-butane is sent via line 1 to a de-isobutanizer 10. The rich normal-butane cut effluent is sent via line 11 to the normal-butane cracking furnace 15. An ethane fraction is sent via line 2 to the ethane cracking furnace 16. The cracked products are sent via lines 21 and 22 to the quench tower 23 and subsequently to the compressors 31-35, then through driers 36 to the de-methanizer 40. The lights are sent via line 41 to the PSA 42 (pressure swing adsorption) to separate methane and hydrogen. The bottoms of the de-methanizer 40 are sent via line 43 to the de-ethanizer 50. The overhead of de-ethanizer 50, a mixture essentially of ethylene and ethane, is sent via line 51 through an acetylene converter 52 to a C2-splitter 60. Ethylene is recovered via line 61 and ethane is recycled via line 62 to the ethane cracking furnace 16. A part of the ethylene produced is sent via line 63 to the metathesis reactor 100. Bottoms of the de-ethaniser 50 are sent via line 53 to a catalytic de-propaniser 70 in which MAPD (methyl acetylene and propadiene) and at least a part of the dienes and alkynes having four or more carbons are substantially hydrogenated into the corresponding olefins. Overhead of de-propanizer 70 is sent via line 71 to a C3-splitter 85 to recover propylene on top and propane at the bottom. Propane can be either recycled to the steamcracking furnace or sold to the LPG market. The bottoms of the catalytic de-propanizer 70 are sent via line 72 to the de-butaniser 80. The raw C4 fraction, produced as overhead of the de-butaniser column 80 is sent via line 81 to an hydrogenation section 90-95 to be selectively hydrogenated to convert the remaining dienes and alkynes into butenes. After the first selective hydrogenation reactor 90, part of the reactor effluent can be recycled through line 91 in order to control the inlet concentration of dienes and alkynes. The remaining effluent of the reactor 90 flows through line 93 to the finishing selective hydrogenation reactor 94. The effluent of reactor 94 is sent via line 95 and mixed with ethylene of line 63 to enter the metathesis reactor 100 to produce propylene. The metathesis section can contain optionally pretreaters in order to remove possible contaminants in the feed to the metathesis reactor. The product of the metathesis reactor is fractionated in a de-propaniser 110. The overhead product 111 is cooled down to create a reflux stream 112. Part of the condensed reflux stream can be pumped and sent via line 113 to the inlet of the de-ethaniser 50 of the steamcracker complex. The light olefin vent stream (C2 vent recycle) can flow via line 114 to the inlet of the fourth stage compressor of the steamcracker complex. The bottoms of the de-propanizer 110 are sent via line 115, as well as heavies from the de-butanizer 80, via line 82 to a full hydrogenation unit 120 and then recycled via line 121 to the normal-butane cracking furnace, optionally through the de-isobutanizer 10.

FIG. 2-10 disclose alternative flow-schemes according to the invention.

Figure 2:
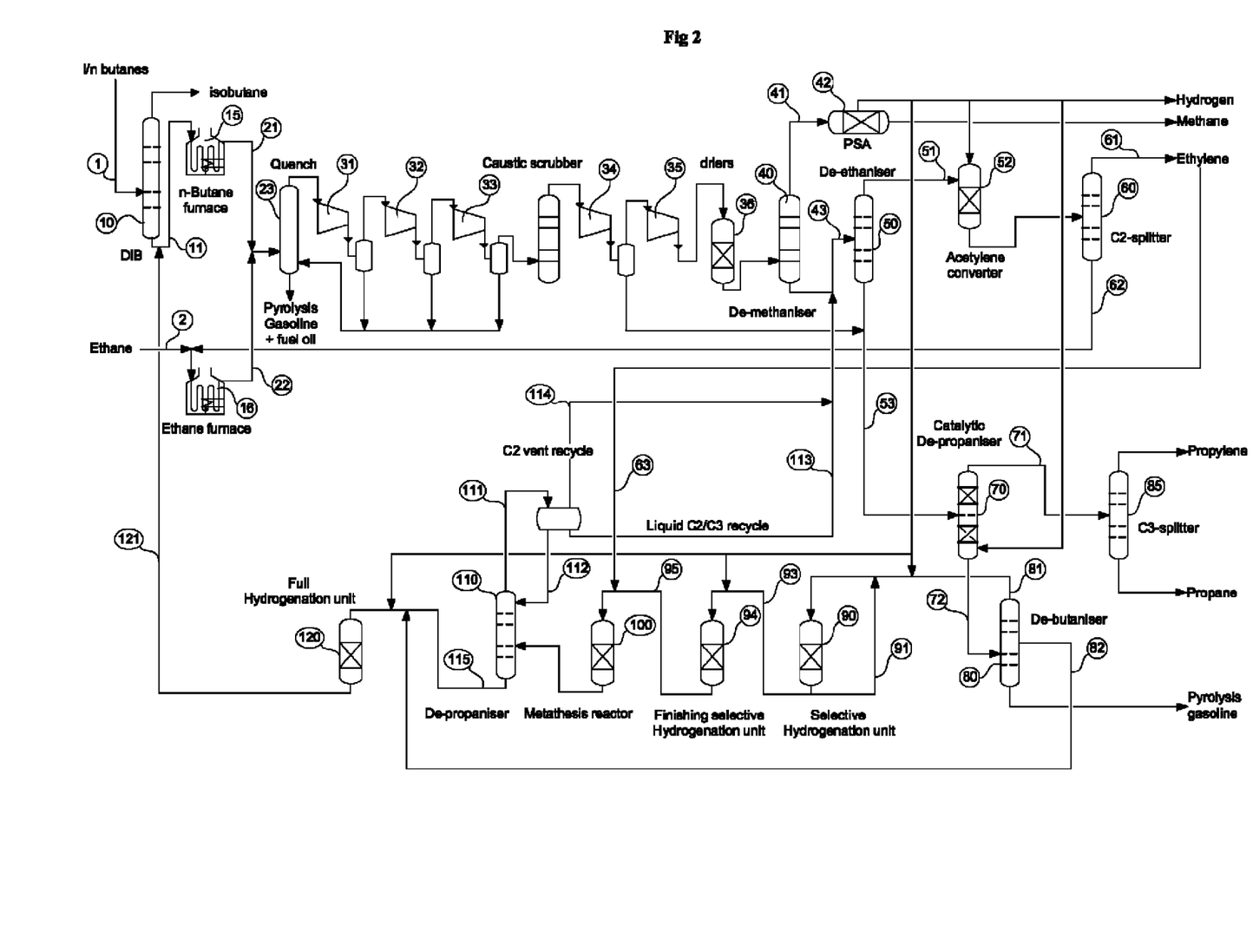

FIG. 2: De-Methaniser-First.

This scheme represents a similar scheme as in FIG. 1, except that the de-propaniser 110 works at a sufficient high pressure as to sent the C2 vent recycle stream 114 to the inlet of the de-ethaniser 50.

Figure 3:
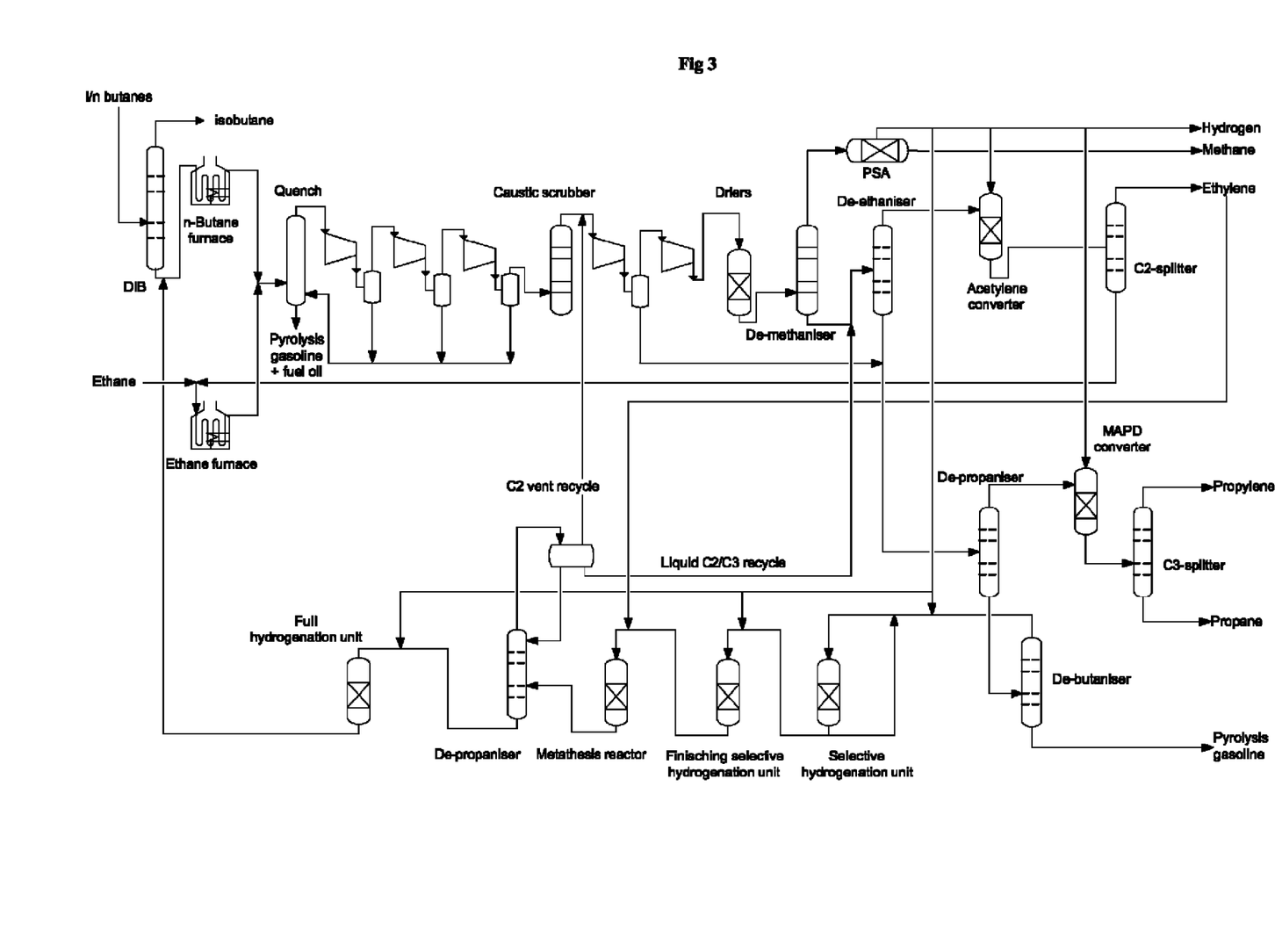

FIG. 3: De-Methaniser-First.

This scheme represents a similar scheme as in FIG. 1, except that no heavies from the de-butaniser are recycled to the full hydrogenation unit and except that the non-catalytic cracking complex consist of a separate de-propaniser and MAPD converter.

Figure 4:
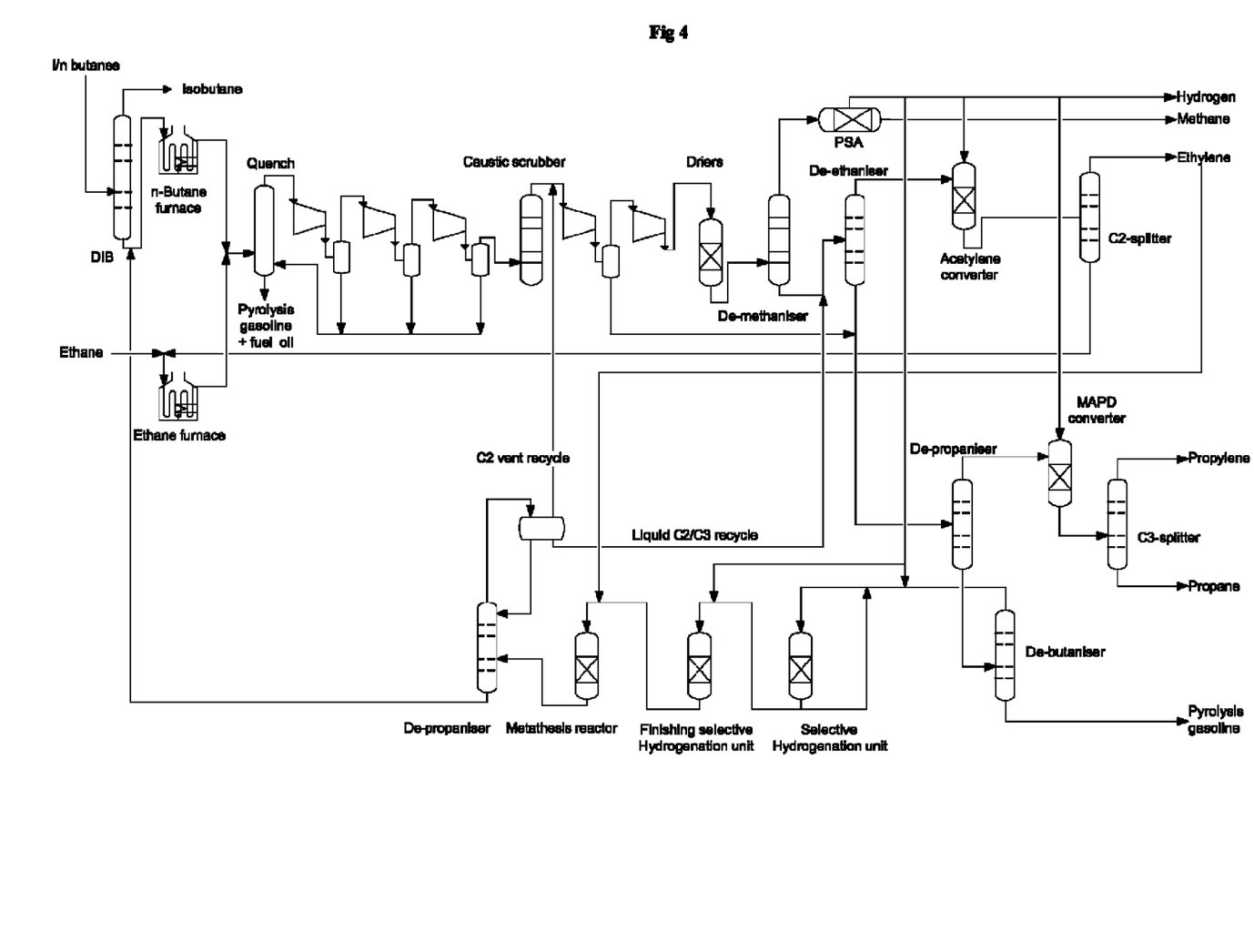

FIG. 4: De-Methaniser First.

This scheme represents a similar scheme as in FIG. 3, except that the bottom product of the de-propaniser downstream of the metathesis unit is recycled as such without full hydrogenation to the cracking zone.

Figure 5:
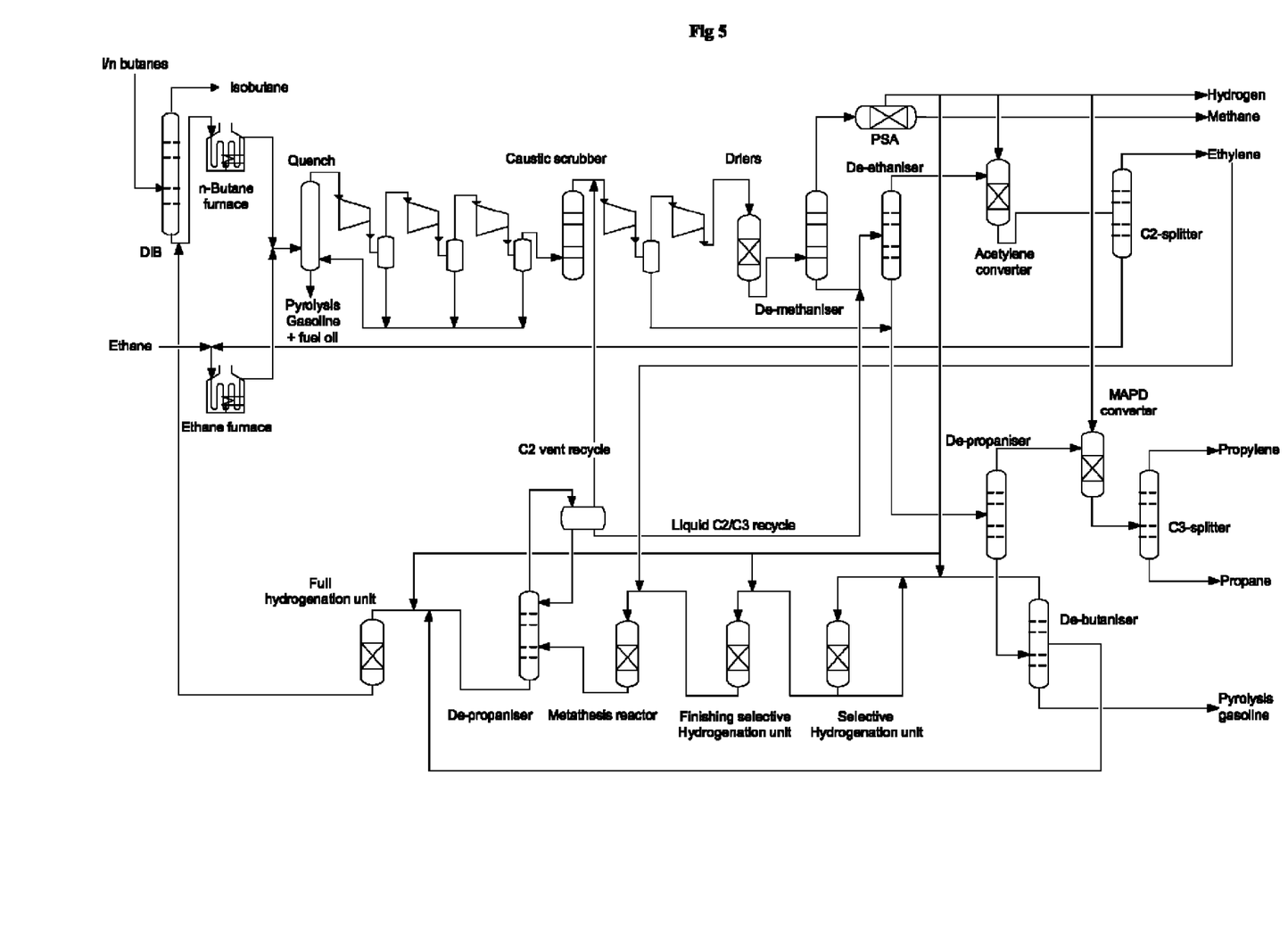

FIG. 5: De-Methaniser First.

This scheme represents a similar scheme as in FIG. 1, except that the non-catalytic cracking complex consists of a separate de-propaniser and MAPD converter.

Figure 6:
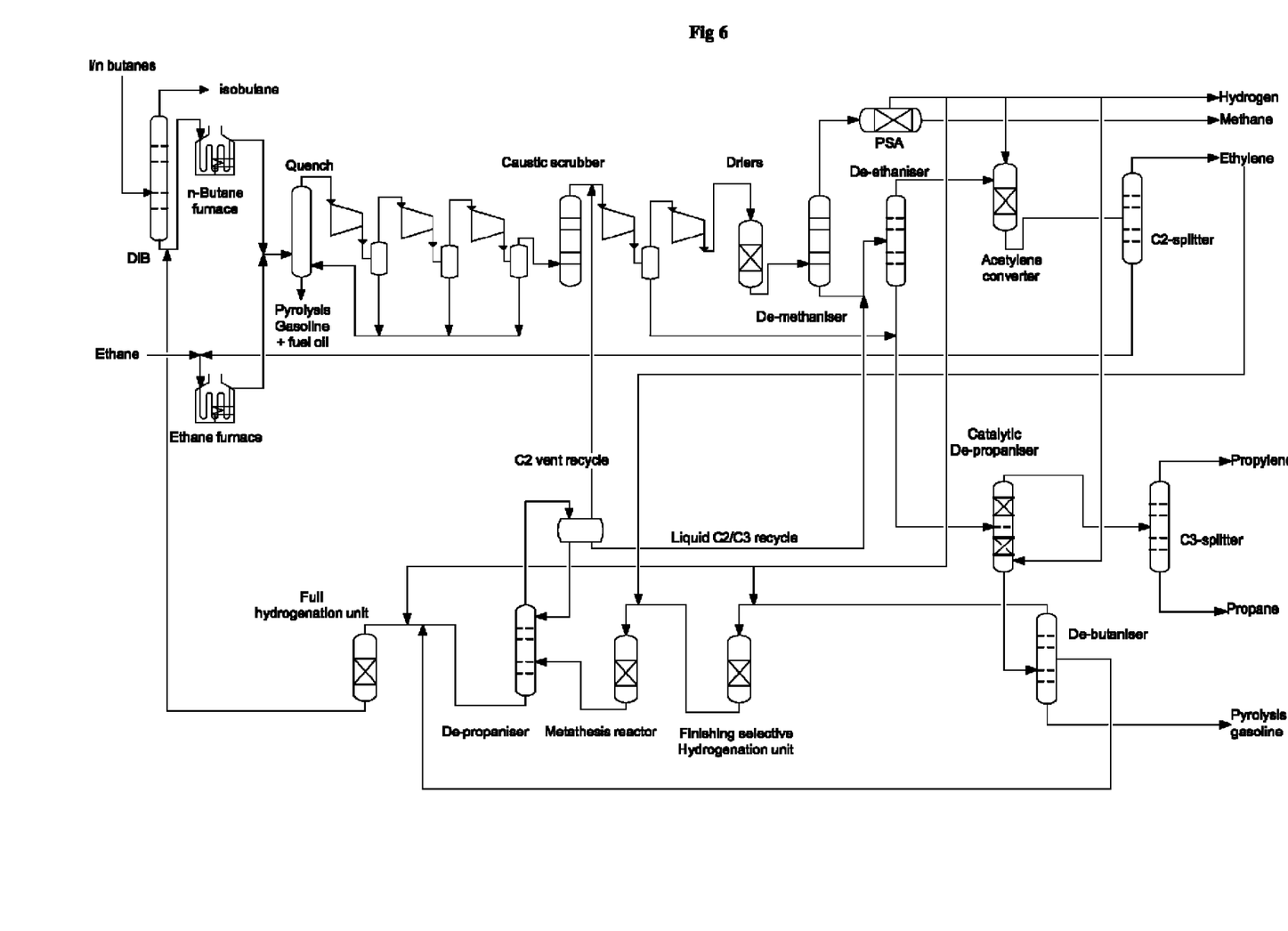

FIG. 6: De-Methaniser First.

This scheme represents a similar scheme as in FIG. 1, except that only a finishing hydrogenation unit is required for the conversion of remaining dienes and alkynes having 4 carbons in the raw C4 stream as most of them are converted in the catalytic de-propaniser.

Figure 7:
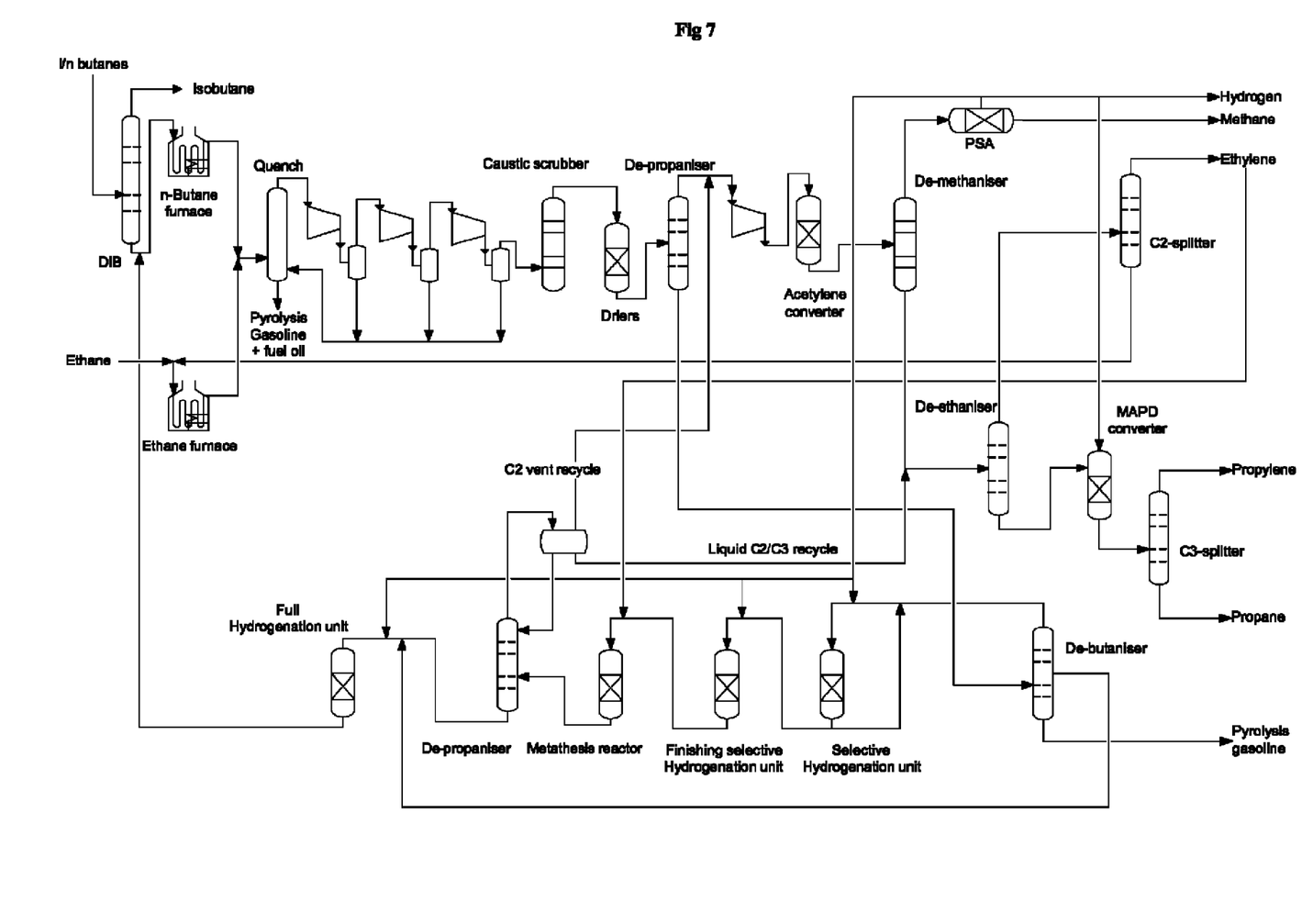

FIG. 7: De-Propaniser First.

After the third compressor stage, the C3's and lighter are separated in a de-propaniser. The overhead is further compressed in the last stage compressor and flows to a front-end acetylene converter. In this acetylene converter substantially all the acetylene is hydrogenated and at least a part of the MAPD is also hydrogenated. The MAPD converter after the de-ethaniser is in this case a finishing converter.

Figure 8:
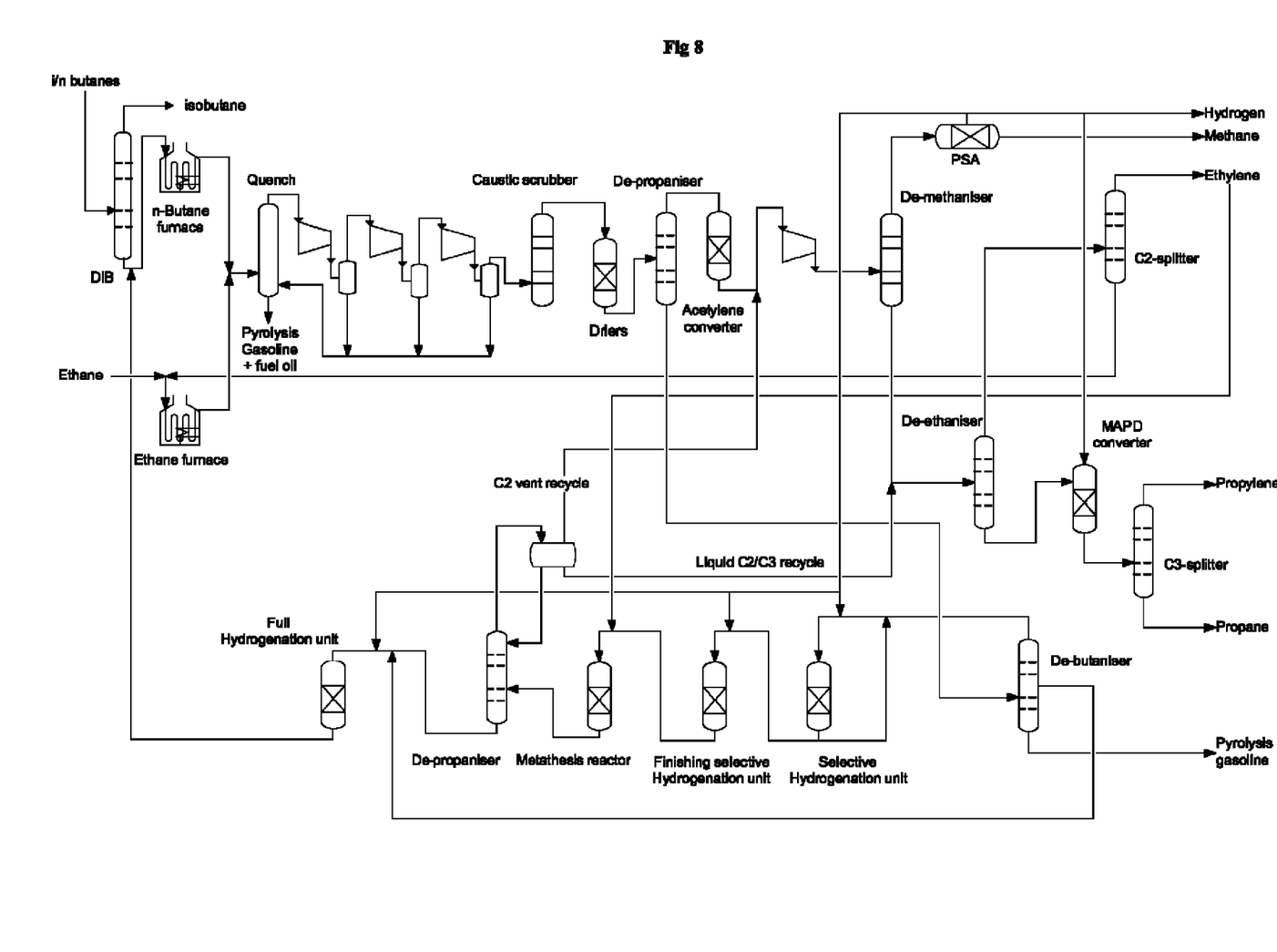

FIG. 8: De-Propaniser First.

This scheme represents a similar scheme as in FIG. 7, except that the front-end acetylene converter is located before the last stage compressor. This allows recycling the C2 vent from the de-propaniser after the metathesis reactor downstream of the acetylene converter.

Figure 9:
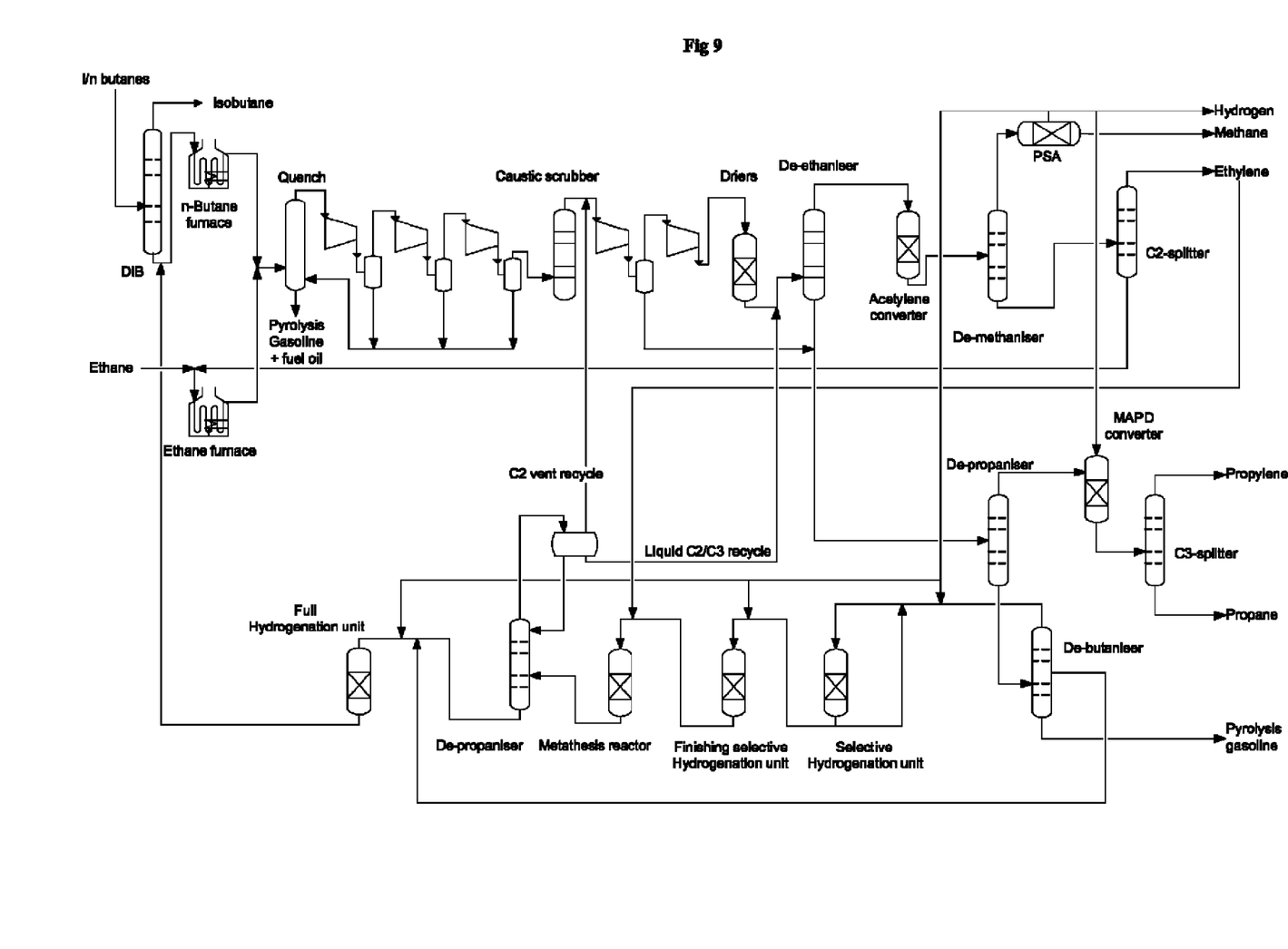

FIG. 9: De-Ethaniser First.

This scheme represents a similar scheme as in FIG. 5, except that the de-ethaniser is located directly after the compression section and driers. The de-ethaniser is followed by a front-end acetylene converter that only treats the acetylene.

Figure 10:
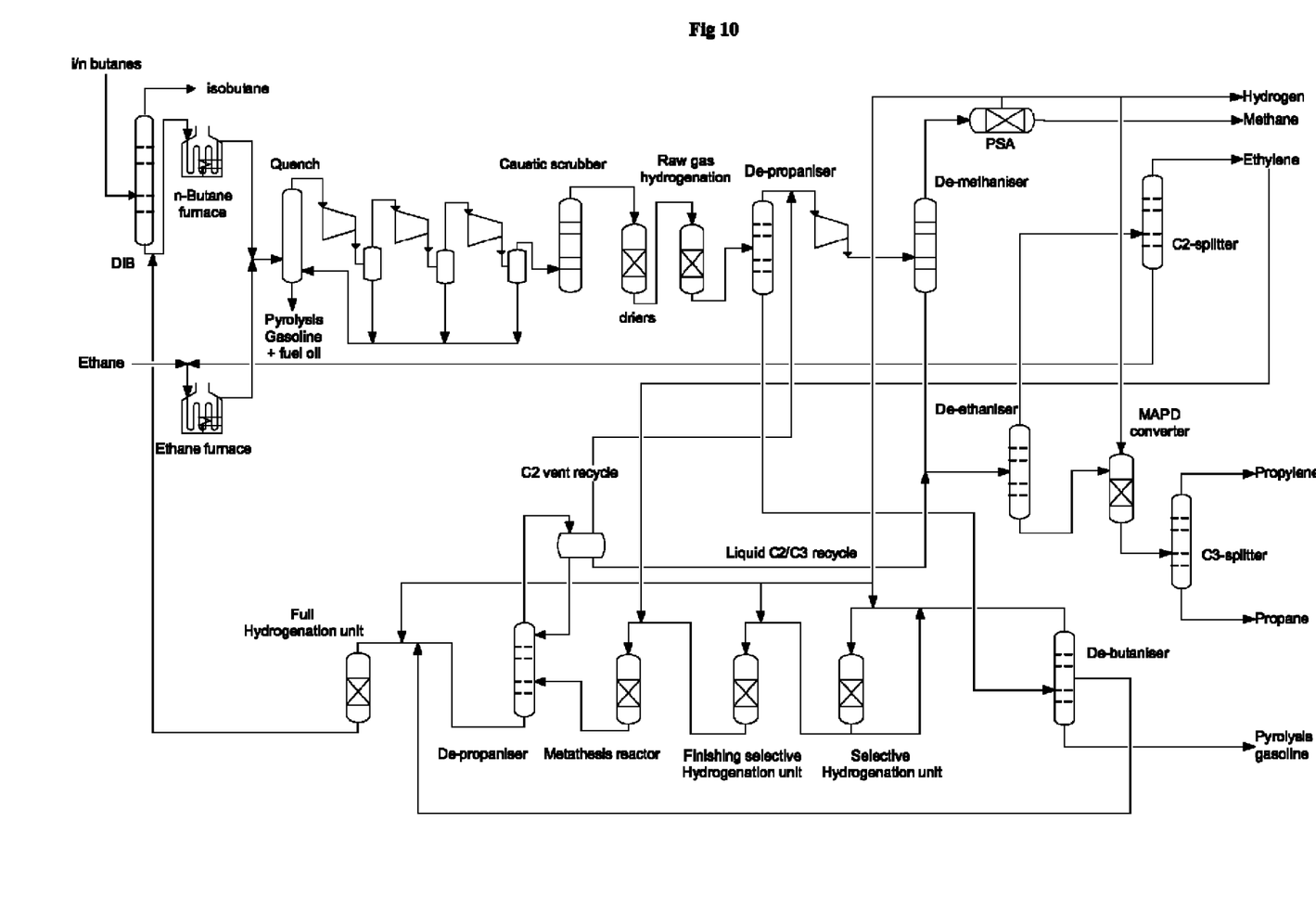

FIG. 10: De-Propaniser First.

This scheme represents a similar scheme as in FIG. 8, except that the acetylene conversion occurs in a raw gas hydrogenation unit, treating the raw gas coming from the driers. Substantially all acetylene and part of the dienes and alkynes having 3 or more hydrocarbons are hydrogenated in their corresponding olefins.

These flow-schemes are only given as examples and are not limiting. Those skilled in the art will understand that depending on the maximum allowable operating pressure of certain distillation columns that depends directly on the concentration of reactive molecules like dienes and alkynes, the recycle streams downstream of the metathesis unit can be sent to appropriate distillation columns working at higher pressure and hence shorten the recycle loop.

In table 1 are the cracking products of various hydrocarbons from a steamcracker.

TABLE 1

| Test Feed | Ethane | Ethane | Propane | Propane | nButane | nButane | isoButane | isoButane |
|---|---|---|---|---|---|---|---|---|
| Feed conversion | 65% | 75% | 85% | 95% | 85% | 95% | 85% | 95% |
| Products | | | | | | | | |
| Hydrogen | 4.03 | 4.61 | 1.38 | 1.60 | 0.81 | 1.04 | 1.10 | 1.24 |
| Methane | 4.10 | 6.18 | 21.12 | 25.90 | 17.31 | 20.95 | 18.91 | 24.49 |
| Acetylene | 0.32 | 0.57 | 0.37 | 0.78 | 0.19 | 0.43 | 0.18 | 0.40 |
| Ethylene | 51.46 | 56.60 | 34.42 | 39.85 | 31.88 | 38.74 | 8.09 | 12.40 |
| Ethane | 35.07 | 24.99 | 3.40 | 3.41 | 4.46 | 4.41 | 1.14 | 1.55 |
| Propyne | 0.02 | 0.04 | 0.35 | 0.49 | 0.28 | 0.44 | 1.12 | 1.85 |
| Propylene | 1.20 | 1.40 | 16.96 | 11.92 | 21.13 | 16.44 | 22.60 | 20.61 |
| Propane | 0.17 | 0.20 | 15.05 | 5.12 | 0.51 | 0.44 | 0.33 | 0.28 |
| Vinyl acetylene | 0.04 | 0.09 | 0.03 | 0.12 | 0.01 | 0.06 | 0.01 | 0.02 |
| Butadiene | 1.24 | 1.72 | 2.13 | 3.05 | 2.31 | 3.36 | 1.21 | 1.99 |
| Butene-1 | 0.10 | 0.10 | 0.76 | 0.52 | 1.38 | 0.97 | 0.89 | 0.96 |
| IsoButene | 0.00 | 0.00 | 0.16 | 0.13 | 0.16 | 0.17 | 19.93 | 14.45 |
| Butene-2 | 0.08 | 0.09 | 0.23 | 0.20 | 0.70 | 0.52 | 0.24 | 0.30 |
| IsoButane | 0.00 | 0.00 | 0.03 | 0.01 | 0.03 | 0.02 | 14.99 | 5.00 |
| nButane | 0.39 | 0.29 | 0.03 | 0.02 | 14.99 | 5.03 | 0.01 | 0.01 |
| C5+ | 1.73 | 3.01 | 3.51 | 6.72 | 3.78 | 6.88 | 9.21 | 14.35 |
| C5 | 0.48 | 0.55 | 1.10 | 1.10 | 1.49 | 1.65 | 2.34 | 2.47 |
| C6 non ar. | 0.03 | 0.04 | 0.18 | 0.13 | 0.32 | 0.25 | 1.35 | 1.21 |
| Benzene | 0.85 | 1.58 | 1.39 | 3.15 | 1.21 | 2.91 | 2.39 | 5.14 |
| C7 non ar. | 0.01 | 0.01 | 0.04 | 0.03 | 0.09 | 0.07 | 0.64 | 0.41 |
| Toluene | 0.10 | 0.18 | 0.35 | 0.73 | 0.34 | 0.77 | 1.47 | 2.57 |
| C8 non ar. | 0.00 | 0.00 | 0.00 | 0.00 | 0.01 | 0.00 | 0.08 | 0.03 |
| C8 aro | 0.08 | 0.22 | 0.14 | 0.47 | 0.12 | 0.38 | 0.43 | 0.91 |
| C9 and heavier | 0.17 | 0.44 | 0.29 | 1.11 | 0.21 | 0.85 | 0.50 | 1.61 |

The invention claimed is:

1. A process for the selective production of olefins from light hydrocarbons comprising:
    fractionating a butane fraction in a de-isobutanizer to obtain an enriched iso-butane fraction and an enriched normal-butane fraction;
    cracking the enriched normal-butane fraction and optionally a second fraction selected from an ethane fraction, a propane fraction and combinations thereof in a non-catalytic cracking zone to produce an olefin rich stream;
    treating the olefin rich stream in a separating section, wherein the treating comprises:
        removing hydrogen and methane from the olefin rich stream; recovering a first ethylene stream, a first propylene stream, a propane stream, a first $C_4$ stream and an ethane stream; recycling the ethane stream and optionally the propane stream to the non-catalytic cracking zone; removing heavies from the olefin rich stream;
    selectively hydrogenating dienes and alkynes in the first $C_4$ stream into their corresponding olefins to form a hydrogenated $C_4$ stream;
    reacting by metathesis in a metathesis section the hydrogenated $C_4$ stream and at least a portion of the first ethylene stream to form an effluent comprising propylene; and
    treating the effluent to recover a second ethylene stream, a second propylene stream, a second $C_4$ stream and a heavies stream.

2. The process of claim 1, wherein ethane and butane are cracked in the non-catalytic cracking zone.

3. The process of claim 1, wherein a light hydrocarbon feedstock comprising ethane, propane and butane is fractionated to obtain a C3 fraction used as LPG, an ethane fraction and a butane fraction, said butane fraction is sent to the cracking zone through the de-isobutanizer and said ethane fraction is sent to the cracking zone.

4. The process of claim 1, further comprising transforming the enriched iso-butane in iso-butene and subsequently in poly-iso-butene, di-iso-butene and alkylate for gasoline blending.

5. The process of claim 4, further comprising reacting t-butyl-ethers, methyl-metacrylate or combinations thereof with formaldehyde to form isoprene.

6. The process of claim 1, further comprising cracking enriched normal-butane fraction and each of the optional second fractions in separate non-catalytic cracking zones.

7. The process of claim 1 further comprising treating the second $C_4$ stream.

8. The process of claim 1 further comprising recycling the second C4 stream to the non-catalytic cracking zone through a de-isobutanizer.

* * * * *